(12) United States Patent
Wall (10) Patent No.: US 12,023,433 B2
(45) Date of Patent: Jul. 2, 2024

(54) WOUND DRESSING APPARATUS

(71) Applicant: Phase One Health, LLC, Nashville, TN (US)

(72) Inventor: Billy Russell Wall, Arrington, TN (US)

(73) Assignee: Phase One Health, LLC, Nashville, TN (US)

( * ) Notice: Subject to any disclaimer, the term of this patent is extended or adjusted under 35 U.S.C. 154(b) by 0 days.

(21) Appl. No.: 18/076,181

(22) Filed: Dec. 6, 2022

(65) Prior Publication Data
US 2023/0173162 A1 Jun. 8, 2023

Related U.S. Application Data

(63) Continuation of application No. 16/917,072, filed on Jun. 30, 2020, now Pat. No. 11,517,655, which is a continuation of application No. 14/378,309, filed as application No. PCT/US2013/025875 on Feb. 13, 2013, now Pat. No. 10,695,471.

(60) Provisional application No. 61/633,509, filed on Feb. 13, 2012.

(51) Int. Cl.
*A61M 1/00* (2006.01)
*A61F 13/05* (2024.01)
*A61H 9/00* (2006.01)

(52) U.S. Cl.
CPC ............... *A61M 1/85* (2021.05); *A61F 13/05* (2024.01); *A61H 9/0057* (2013.01); *A61H 9/0078* (2013.01); *A61M 1/90* (2021.05); *A61M 1/912* (2021.05); *A61M 1/915* (2021.05); *A61M 1/92* (2021.05); *A61M 2202/0208* (2013.01); *F04C 2270/0421* (2013.01)

(58) Field of Classification Search
CPC ............ A61M 1/00; A61M 1/90; A61M 1/91; A61M 1/912; A61M 1/915; A61M 1/92; A61M 1/94; A61M 2022/0208; A61H 9/0057; A61H 9/0078; A61H 2201/16; A61H 2201/5056; A61F 13/00; A61F 2220/00; A61F 5/0601; A61F 9/00068
See application file for complete search history.

(56) References Cited

U.S. PATENT DOCUMENTS

| | | | | |
|---|---|---|---|---|
| 2,280,915 A | * | 4/1942 | Johnson | A61F 13/00068 604/179 |
| 4,250,882 A | * | 2/1981 | Adair | A61M 1/98 604/355 |
| 8,945,030 B2 | * | 2/2015 | Weston | A61M 1/982 604/289 |
| 10,695,471 B2 | * | 6/2020 | Wall | A61M 1/92 |
| 11,517,655 B2 | * | 12/2022 | Wall | A61F 13/00068 |
| 2005/0148913 A1 | * | 7/2005 | Weston | A61M 1/964 602/2 |

(Continued)

*Primary Examiner* — Colin W Stuart
*Assistant Examiner* — Douglas Y Sul
(74) *Attorney, Agent, or Firm* — Jacob W Neu; Bradley Arant Boult Cummings, LLP (57) ABSTRACT

The wound dressing apparatus facilitates administration of combined negative pressure and positive pressure treatment at a wound site. The wound dressing apparatus includes a wound dome having a substantially hollow dome interior, a manifold that is in fluid communication with the dome interior, a first passage adapted to connect to a negative pressure source to the dome interior, and a second passage adapted to connect to a positive pressure source to the manifold.

18 Claims, 10 Drawing Sheets

(56) References Cited

U.S. PATENT DOCUMENTS

| | | | |
|---|---|---|---|
| 2007/0141128 A1* | 6/2007 | Blott | A61M 1/92 424/94.64 |
| 2007/0191754 A1* | 8/2007 | Aali | A61F 15/008 602/41 |
| 2009/0264838 A1* | 10/2009 | Livne | A61M 1/915 604/290 |
| 2011/0004168 A1* | 1/2011 | Eriksson | A61F 13/00068 604/290 |
| 2013/0053795 A1* | 2/2013 | Coulthard | A61F 13/00068 604/319 |

* cited by examiner

WOUND DRESSING APPARATUS

TECHNICAL FIELD

The present disclosure relates to a wound dressing apparatus for use in wound care treatment. More particularly, the present disclosure pertains to a wound dressing apparatus for providing combined negative and positive pressure treatment to a wound site.

BACKGROUND ART

Chronic and acute wounds, including pressure ulcers, diabetic wounds, and burns, present significant challenges to the health care industry. Patient care providers are actively seeking methods, devices, and systems for treating such wounds at a lower cost and with greater efficacy.

Conventional treatments for chronic wounds typically include negative pressure therapy and/or hyperbaric oxygen therapy.

Negative pressure therapy is the controlled application of sub-atmospheric pressure to a wound using a therapy unit, such as a vacuum or suction device, to expose the wound to negative pressure to help promote wound healing. The wound is typically covered to facilitate the application of negative pressure and suction at the wound area. Various types of resilient, open cell foam surface dressings are typically sealed within an adhesive drape to provide the sub-atmospheric pressure at the wound site. Exudates are drained from the wound site and typically directed to a canister that stores the fluids and/or infectious material until properly disposed. Negative pressure wound therapy is often prescribed for chronic and acute wound types such as diabetic wounds, pressure ulcers, abdominal wounds, trauma wounds, various burns, flaps and grafts. However, negative pressure therapy may be less effective on patients having vascular disorders, such as diabetes, because negative pressure therapy can create a hypoxic environment at the wound. In current hospital settings, portable vacuum pumps are often rented or purchased for the purpose of providing negative pressure therapy. This can significantly increase the cumulative costs of providing wound care.

Hyperbaric oxygen therapy is the controlled application of oxygen to a wound at greater-than-atmospheric pressure(s). Oxygen is typically required for all new cell growth. Chronic or non-healing wounds tend to exhibit low oxygen tensions, or tend to be ischemic. A wound can become dormant if the amount of poorly oxygenated wound tissue reaches a critical mass. In this state, the body may no longer recognize the need to heal the affected area, thereby exacerbating the lack of oxygen in the wound and impairing healing of the wound by the body. Oxygen therapy is particularly useful for patients with poor circulation. The oxygen helps to kill bacteria and when applied to an open wound at a hyperbaric level, the oxygen is dissolved into the wound and absorbed by the surface wound tissue. The cells of the wound tissue that absorb the oxygen will begin metabolic activity in response to the increased oxygen tension. When the oxygen source is removed, the previously active cells request more oxygen from the body. The body responds by beginning to form new blood cells, and thus, starting the healing process. Accordingly, when delivered to a wound site under hyperbaric conditions, oxygen may act as a primary wound treatment fluid Typically, hyperbaric oxygen therapy is delivered by placing the patient in a hyperbaric chamber that encompasses the full body of the patient or an entire extremity, such as a leg or an arm. Such chambers are problematic due to their lack of portability, the difficulty in sterilization of the chambers between patients, and the potential adverse effects of breathing oxygen at hyperbaric pressure. Preferably, hyperbaric oxygen treatment should be localized at the wound site rather than applied to the patient's entire body or extremity.

While both negative pressure and hyperbaric oxygen therapies are each believed to be effective when administered as separate wound care treatments, many patients may benefit from a treatment protocol incorporating both negative pressure and hyperbaric oxygen therapies. Because existing hyperbaric oxygen treatment is typically performed in a hyperbaric chamber, switching between negative pressure therapy and hyperbaric oxygen therapy is time-consuming. Before entering a hyperbaric oxygen chamber, a patient must first be disconnected from the negative therapy device. The negative pressure therapy dressing, which typically includes packing materials, a drain, tubing, and sealing material, must then be removed. Following hyperbaric oxygen treatment, a new negative pressure dressing would have to be applied. These procedures are wasteful and time-consuming, making it difficult, if not impossible, to alternate between negative pressure therapy and hyperbaric oxygen therapy every few minutes or less.

More recently, wound care systems and methods have been developed that combine negative and positive pressure (e.g. hyperbaric oxygen) wound treatment therapies. Such methods and systems are described, for example, in U.S. Pat. No. 7,648,488, issued Jan. 19, 2010; U.S. Pat. No. 8,357,130, issued Jan. 22, 2013; U.S. Patent Publication No. 2008/0140029; and U.S. Patent Publication No. 2010/0121287.

Wound care treatment may be further enhanced by deactivating pathogenic microorganisms within the wound environment and physically removing the deactivated microorganisms and other toxins from the wound site. While antibiotics and other drugs may be effective in destroying bacteria and other pathogens, their activity may disrupt the cell walls of the microorganisms, thereby releasing harmful enzymes and other toxins into the wound environment. These harmful enzymes and toxins must be removed or they may become cytotoxic.

It is also known that when planktonic, free floating, individual microorganisms, like bacteria, attach to a surface and gather in groups within a wound environment, they may produce an extra-cellular matrix called a biofilm. Biofilms are held together and protected by a matrix of excreted polymeric compounds called EPS (exopolysacchride). Biofilms provide a protective environment for microorganisms that exist within the biofilm mass and a level of immunity from antibiotic treatments, except in doses that would be fatal to the patient. Consequently, biofilm microorganisms are not affected by the body's own infection-resistance mechanisms. In addition, bacterial biofilms may impair cutaneous wound healing and reduce topical antibacterial efficiency in healing or treating infected skin wounds.

Hypochlorous acid (HOCl) is an active component found in the human immune system as a natural defense against infection, and thus kills bacteria, fungi and viruses without creating mechanisms for drug resistance. Hypochlorous acid compounds can be a safe, fast acting, broad spectrum antimicrobial for topical application, effective against all groups of hydrophobic, hydrophilic, gram-negative and gram-positive bacteria, and yeast, including *Pseudomonas aeruginosa, Staphylococcus aureus*, and multi-drug resistant organisms like methicillin resistant *Staphylococcus aureus*

(MRSA), and vancomycin resistant enterococci (VRE). In addition, hypochlorous acid compounds rapidly penetrate and disrupt biofilm and eradicate the pathogens, the major factor that inhibits wound healing. Unlike most antibiotics, which can take many hours to work, hypochlorous acid compounds, even at small doses, can help eradicate bacteria, fungi and viruses in minutes. When applied topically within a wound environment, hypochlorous acid compounds immediately disrupt and eradicate the bio-film, which surrounds and deactivates a broad spectrum of pathogenic microorganisms. Hypochlorous acid generally controls the tissue bacterial bio-burden without inhibiting the wound healing process and is also commonly associated with improved wound closure. Accordingly, a wound treatment therapy using a stabilized hypochlorous acid compound has recently been disclosed in U.S. Patent Publication No. 2012/0328680, the entirety of which is hereby incorporated by reference.

What is needed, then, is a wound dressing that can deliver one or more different wound therapies to a wound site.

DISCLOSURE OF THE INVENTION

In various embodiments, the wound treatment apparatus of the present invention may provide, using a unitary dressing apparatus, both negative pressure wound therapy and positive pressure (hyperbaric oxygen) wound therapy to a wound site.

An embodiment of the invention includes a wound dressing comprising a domed chamber having a chamber wall defining a dome apex, a peripheral edge, and a substantially hollow dome interior; a flange extending away from the peripheral edge of the domed chamber; a manifold within the domed chamber, the manifold comprising a plurality of apertures in communication with the dome interior; a first passage having a first end adapted to connect to a negative pressure source and a second end in communication with the dome interior; and a second passage having a first end adapted to connect to a positive pressure source and a second end in communication with the manifold. In some embodiments, the manifold is formed integrally with the domed chamber and/or with the flange. Moreover, in certain embodiments, the manifold has an annular shape.

According to another aspect of the invention, the first passage may extend partially across the chamber wall. Further, the second end of the first passage may connect proximate to the apex of the domed chamber. Additionally, a portion of the first passage and/or a portion of the second passage may be formed integrally with the domed chamber.

In a further aspect, the wound dressing apparatus may comprise a pliable material, such as silicone rubber. And in some embodiments, the wound dressing apparatus may have an adhesive provided on at least a portion of the flange. In certain embodiments, the adhesive is effective to create a seal between the flange and a wound drape.

According to yet another aspect of the invention, the wound dressing apparatus may include a domed chamber having a chamber wall defining a dome apex, a peripheral edge, and a dome interior; a flange extending away from the peripheral edge of the domed chamber; a manifold formed within the domed chamber, the manifold comprising a plurality of channels in communication with the dome interior; a first passage having a first end adapted to connect to a negative pressure source, the first passage comprising a plurality of channels in communication with the dome interior; and a second passage having a first end adapted to connect to a positive pressure source and a second end in communication with the manifold.

In some embodiments of the apparatus, the channels of the manifold are arranged in a fractal pattern. Further, the channels of the first passage may also be arranged in a fractal pattern.

Certain embodiments of the apparatus include a manifold that is formed integrally with the domed chamber, and the manifold may span the circumference of the dome interior.

The above described features and advantages, as well as others, will become more readily apparent to those of ordinary skill in the art by reference to the following detailed description and accompanying drawings.

BRIEF DESCRIPTION OF THE DRAWINGS

The wound dressing apparatus may take form in various arrangements of components. The drawings are provided herewith only for purposes of illustrating exemplary embodiments and are not to be construed as limiting the scope of the present disclosure or of the claims appended hereto. The drawings illustrate embodiments of the wound dressing apparatus, in which:

BEST MODE FOR CARRYING OUT THE INVENTION

It is to be understood that both the foregoing general description and the following detailed description present embodiments of the invention and are intended to provide an overview or framework for understanding the nature and character of the invention as it is claimed. The description serves to explain the principles and operations of the claimed subject matter. Other and further features and advantages of the invention will be readily apparent to those skilled in the art upon a reading of the following disclosure.

Reference now will be made in detail to the embodiments of the invention, one or more examples of which are set forth hereinbelow. Each example is provided by way of explanation of the invention and is not a limitation. In fact, it will be apparent to those skilled in the art that various modifications and variations can be made to the teachings of the present disclosure without departing from the scope of the invention. For instance, features illustrated or described as part of one embodiment can be used with another embodiment to yield a still further embodiment.

It is intended that the present disclosure covers such modifications and variations as come within the scope of the appended claims and their equivalents. Other objects, features and aspects of the invention are disclosed in or are obvious from the following detailed description. It is to be understood by one of ordinary skill in the art that the present discussion is a description of exemplary embodiments only and is not intended as limiting the broader aspects of the invention.

All references to singular characteristics or limitations of the invention shall include the corresponding plural characteristic or limitation, and vice versa, unless otherwise specified or clearly implied to the contrary by the context in which the reference is made.

The device(s) of the present disclosure, including components thereof, can comprise, consist of, or consist essentially of the essential elements and limitations of the embodiments described herein, as well as any additional or optional components or limitations described herein or otherwise useful in wound healing application(s).

As used herein, the term(s) "about" or "approximately" should be construed to include both of the numbers specified as the endpoint(s) of any range. Furthermore, any reference to a range should be considered as providing support for any subset within that range.

As used herein, the term "negative pressure" should be construed to include any pressure less than ambient pressure at a wound site. Generally, the negative pressure will be less than the atmospheric pressure at which a patient is located.

As used herein, the term "positive pressure" should be construed to include any pressure greater than ambient pressure at a wound site. Generally, the positive pressure will be greater than the atmospheric pressure at which a patient is located.

As used herein, the term "fluid" should be construed to include any substance lacking a fixed shape, including, but not limited to, any liquid and/or any gas.

As used herein, the term "manifold" should be construed to include a structure or substance that includes one or more channels, passages and/or pathways for distributing fluid.

As used herein, the term "fractal pattern" should be construed to include any geometry or design wherein the similar or identical geometry or design is followed through each branch of the successive stage(s) or division(s) of a branched network. Indeed, a "fractal region" of "fractal pattern" may include equal numbers of bifurcations and junctions disposed serially along a channel, artery, passage and/or pathway in a direction of fluid flow.

Referring now to the drawings, FIGS. 1-7 illustrate an embodiment of the wound dressing apparatus, which is designated generally as reference numeral 10. A wound dressing apparatus can be employed, for example, whenever a controlled distribution and/or collection of fluid(s) is desired. Further, the wound dressing apparatus can be employed whenever combined negative and positive pressure therapy treatment is desired at a wound site.

Wound dressing 10 facilitates both negative pressure wound treatment and positive pressure (hyperbaric) wound treatment at a wound site 2. Further, wound dressing 10 facilitates combined negative pressure therapy and positive pressure therapy at wound site 2.

Wound dressing 10 covers and hermetically seals wound site 2 and facilitates the wound treatment in accordance with the principles and teachings of the wound care system, as described in U.S. Pat. No. 6,648,488 issued Jan. 19, 2010, and U.S. patent application Ser. No. 12/688,485 filed Jan. 15, 2010, and U.S. patent application Ser. No. 12/033,558 filed Feb. 19, 2008, which are all hereby incorporated in their entirety by reference.

Figure 1:
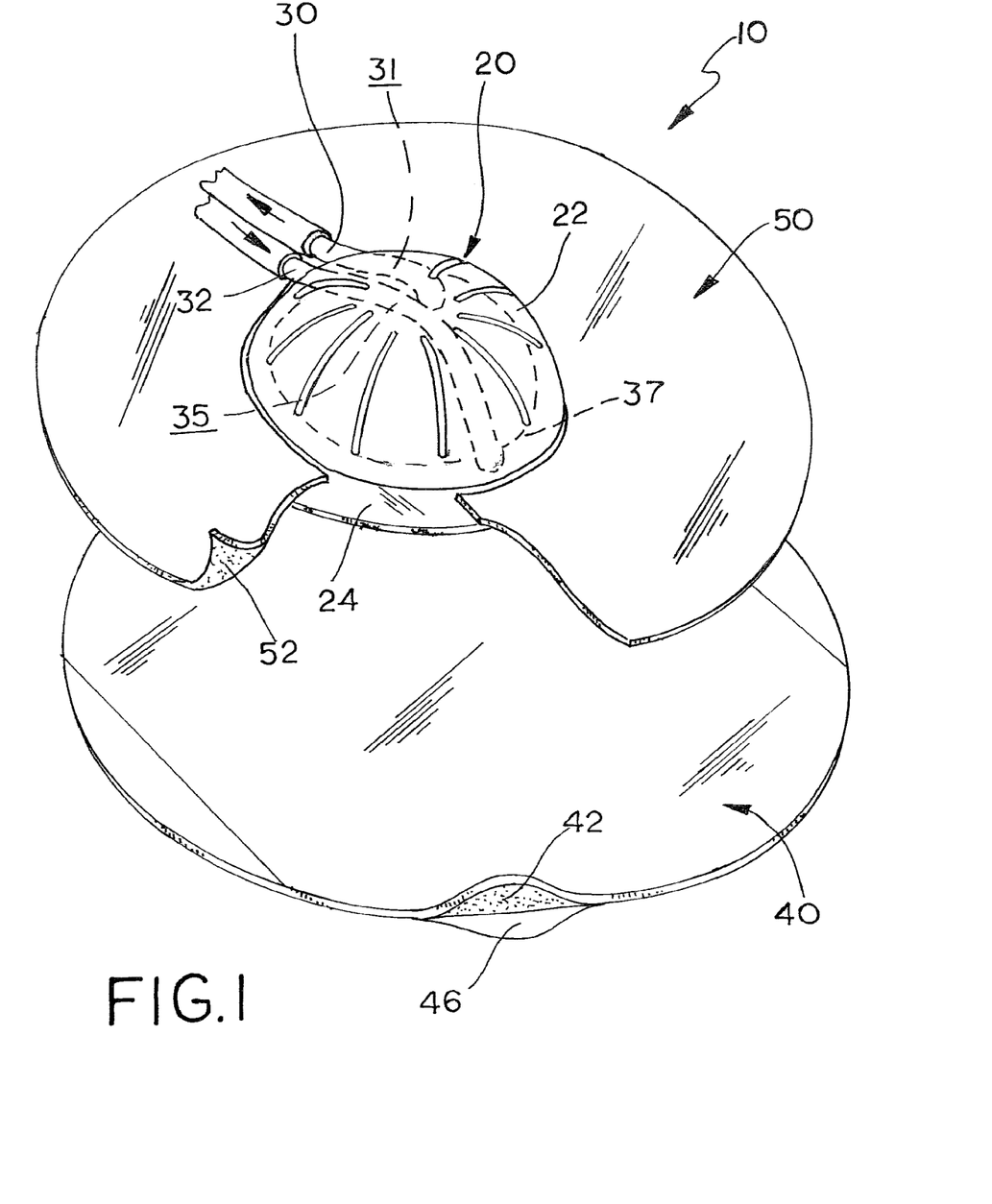
FIG. 1 is a perspective view of an embodiment of the wound dressing apparatus.

As shown in FIG. 1, wound dressing 10 includes a wound dome 20. Wound dome 20 may be formed, molded or otherwise made of a pliable material. The pliable material may be a material suitable for medical purposes, such as a silicon rubber or Arkema Pebax® polymer. Wound dome 20 is configured to have a domed center chamber 22. The domed chamber includes a chamber wall defining a dome apex and a substantially hollow dome interior 21. Further, the wound dome 20 has a peripheral edge and a flange 24. In some embodiments, the domed center chamber 22 further includes an opening 33 at or proximate to the apex. Further, as shown in FIG. 1, domed center chamber 22 may include ribs on the peripheral side wall.

Figure 2:
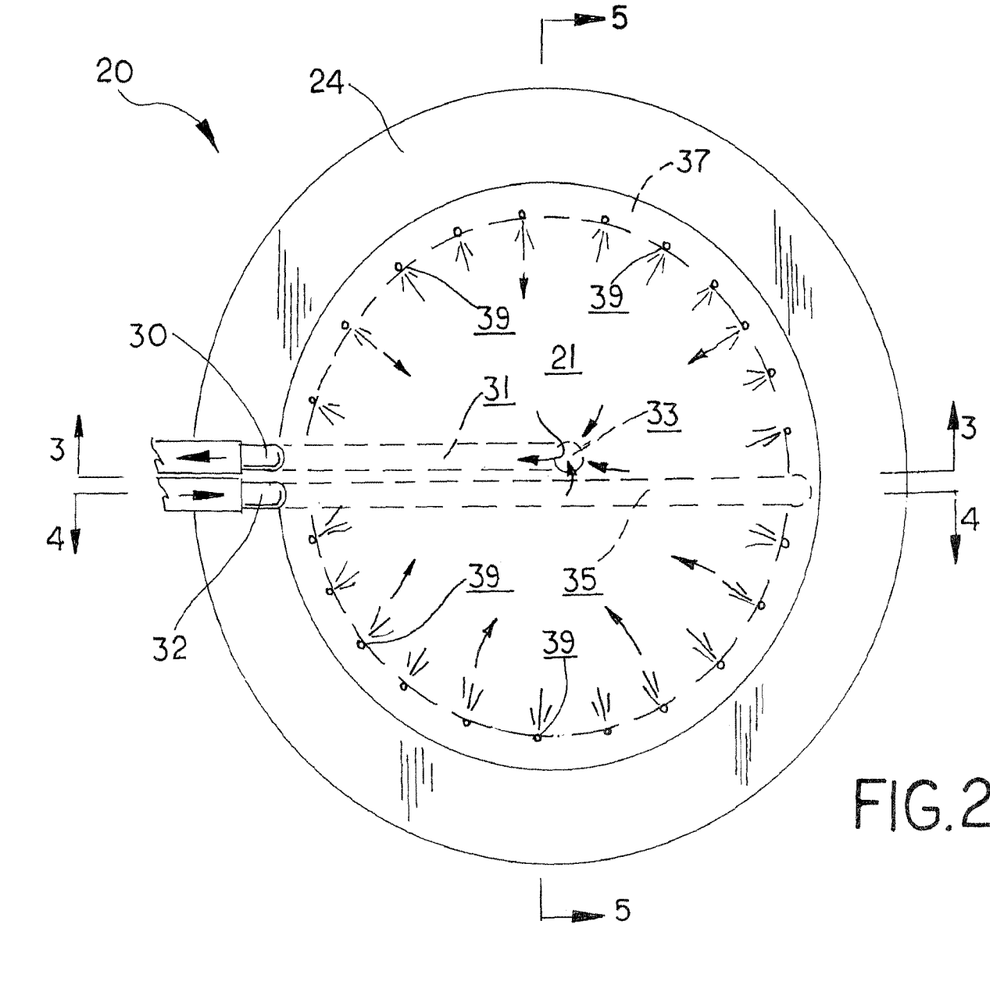
FIG. 2 is a top view of the wound dressing apparatus of FIG. 1.

As illustrated in FIG. 2, flange 24 extends away from a peripheral edge of the domed center chamber 22. The flange is flat in some embodiments of the wound dressing apparatus. In certain embodiments, an adhesive may be provided on at least a portion of a surface of the flange.

Wound dome 20 may have one or more lumen connectors 30 and 32. In certain embodiment, the wound dressing apparatus includes a pair of lumen connectors 30 and 32. The lumen connector(s) may be formed integrally with the dome 20. Lumen connectors 30 and 32 are in open communication with a first passage 31 and with a second passage 35. Lumen connector 30 is adapted to connect to a negative pressure supply and/or a drain line so that the negative pressure draws exudate into fluid passage 31 through opening 33 of domed center 22. The negative pressure supply may be, for example, a therapy unit, such as a vacuum or suction device. Lumen connector 32 is connected to a positive pressure supply and/or to a fluid delivery system and/or to a supply line so that delivered fluids are dispersed radially into the wound site through apertures 39 in manifold 37. In various embodiments of the wound dressing apparatus 10, hypochlorous acid, medications and disinfectants may be introduced into the positive pressure fluid flow and delivered to the wound site through the wound dressing apparatus. In some embodiments, the wound dressing apparatus engages a supply line connected to a fluid source and a drain line connected to a negative pressure source. Negative pressure therapy may be administered to a wound site via the supply line, and hyperbaric fluid therapy may be administered to a wound via the supply line.

A portion of first passage 31 may be formed integrally with domed chamber 22. Likewise, a portion of second passage 35 may be formed integrally with domed chamber 22. Indeed, a portion of first passage 31 and/or a portion of second passage 35 may be formed in the wall of domed chamber 22.

Figure 3:
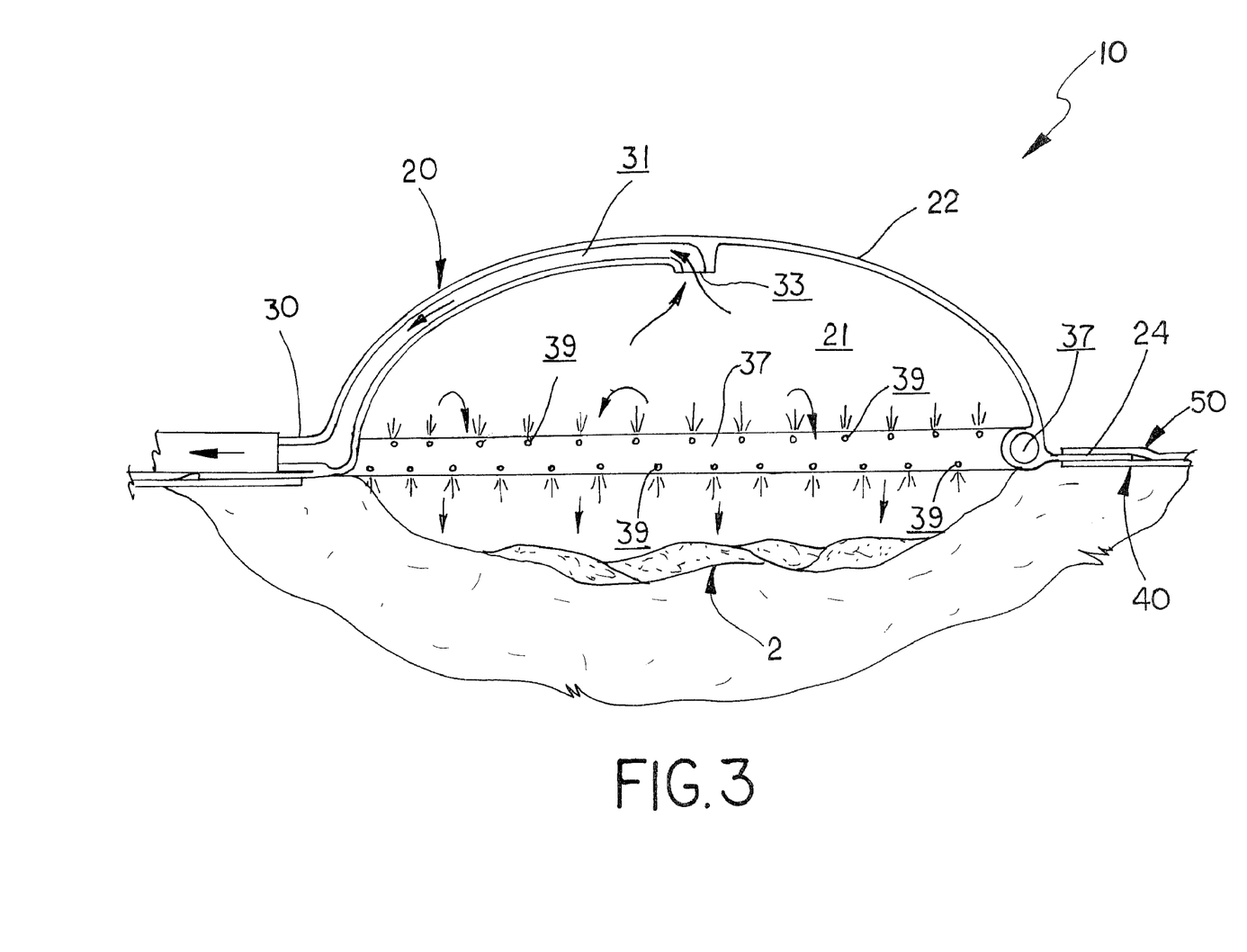
FIG. 3 is a side sectional view of the wound dressing apparatus taken along line 3-3 of FIG. 2.
Figure 9:
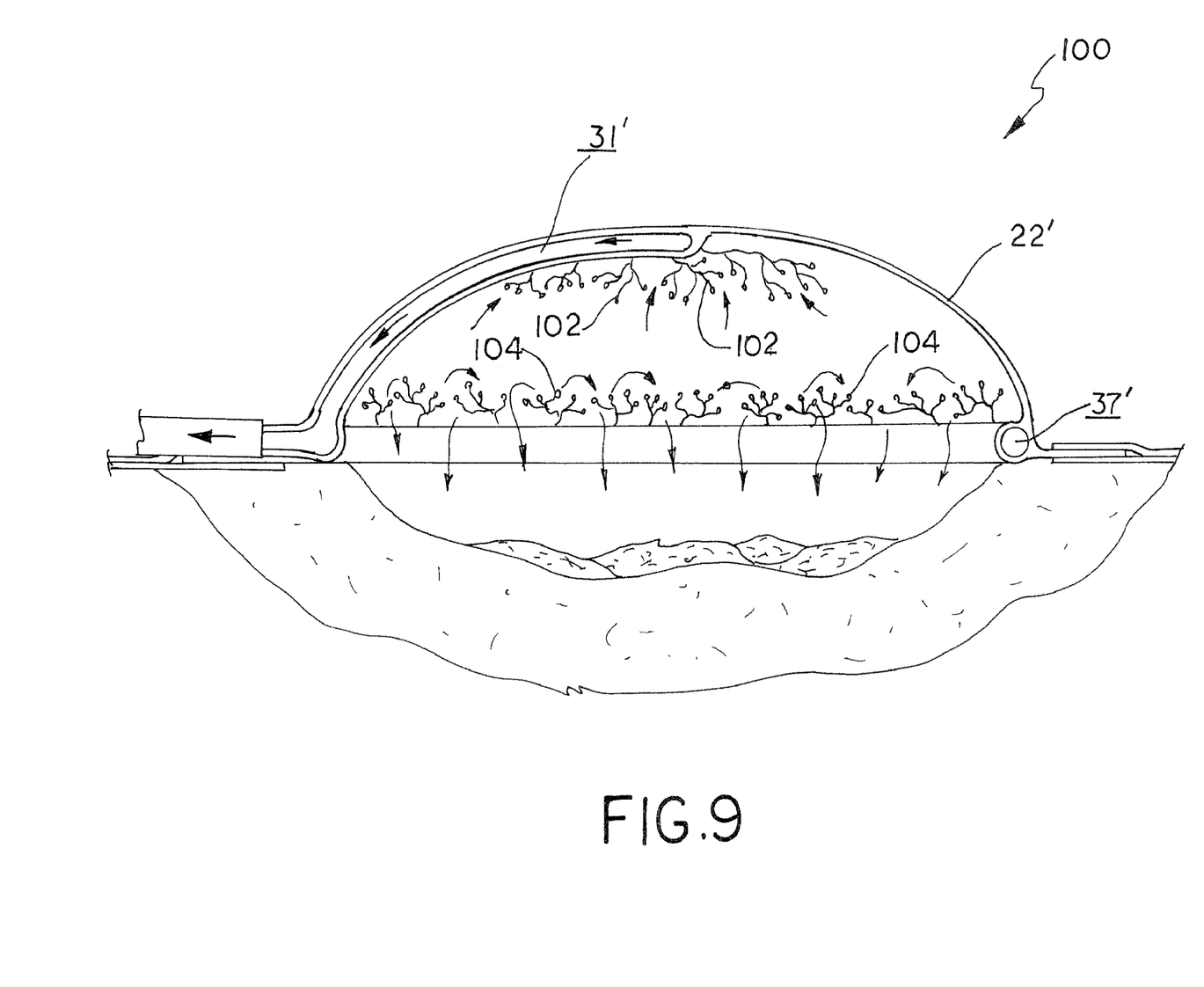
FIG. 9 is a side sectional view of the wound dressing taken along line 9-9 of FIG. 8.
Figure 11:
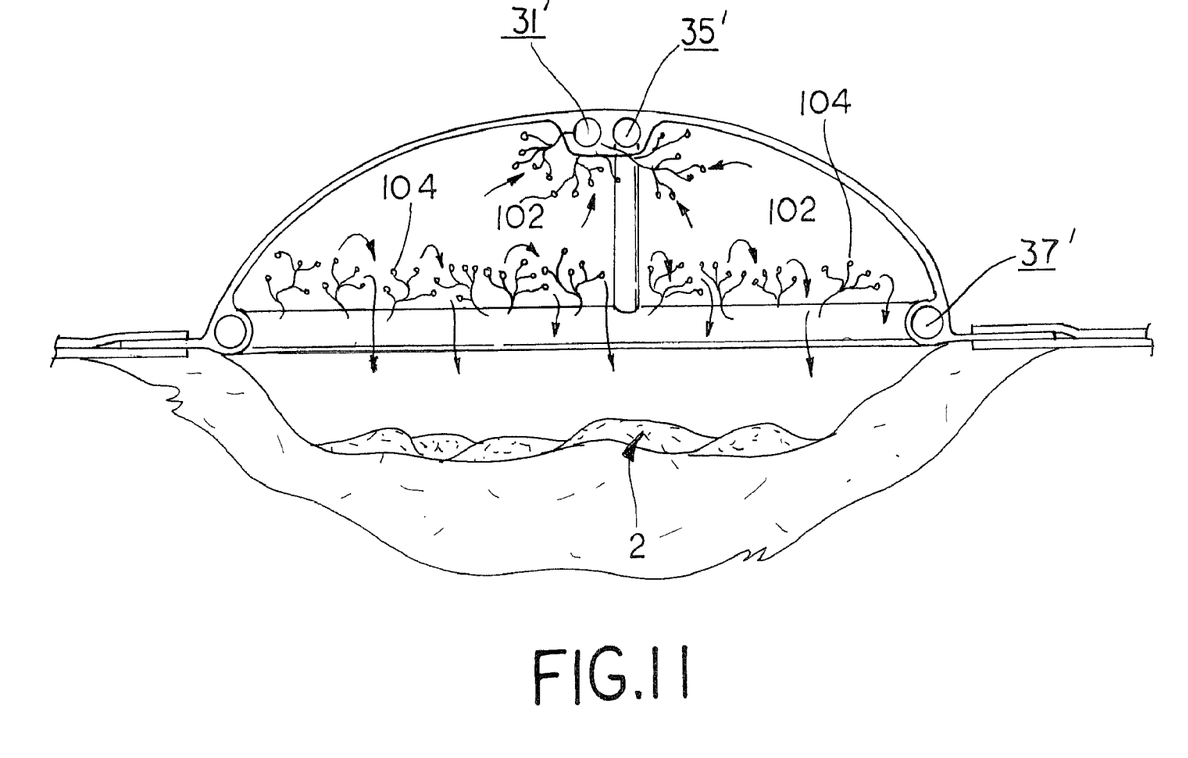
FIG. 11 is an end sectional view of the wound dressing taken along line 11-11 of FIG. 8.

A first end of first passage 31 may be adapted to connect to a negative pressure source and/or to lumen connector 30. A second end of first passage 31 is in open communication with the dome interior 21 and may be connected proximate to the apex of the domed chamber 22. First passage 31 may be adapted or arranged to extend across a portion of the dome chamber 22, as shown in FIG. 1 and in FIG. 3. In certain embodiments, first fluid passage 31 extends from lumen connector 30 to the apex of domed center 22 and terminates in an opening 33 that is in open communication with the interior 21 of wound dome 20, as shown in FIGS. 1, 2 and 3. First passage 31 may comprise a plurality of fluid channels, arteries or pathways 102 that are in communication with the dome interior 21, as shown in FIG. 9 and in FIG. 11. The channels 102 of first passage 31 may be arranged in a fractal pattern.

Figure 4:
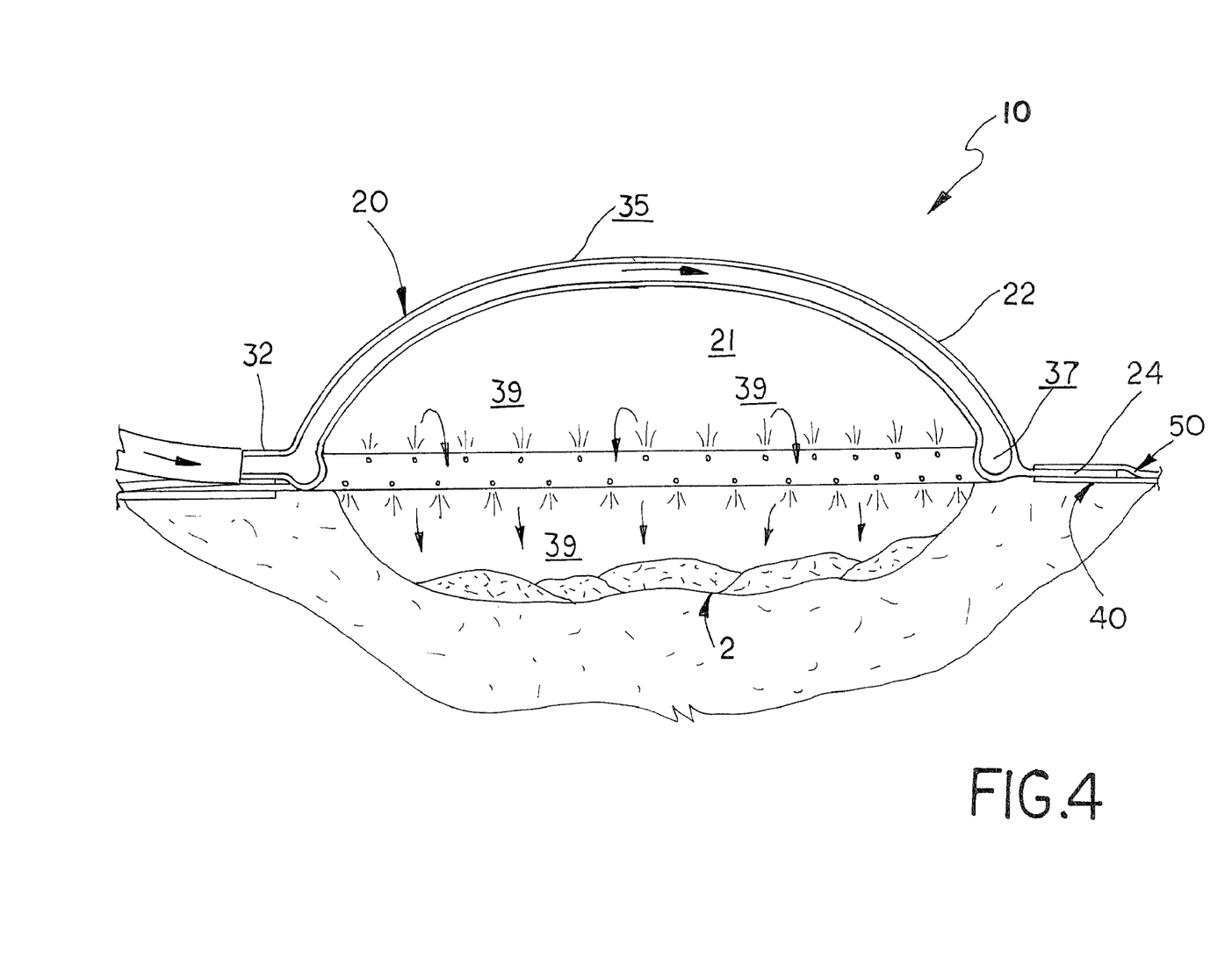
FIG. 4 is a sectional view of the wound dressing taken along line 4-4 of FIG. 2.
Figure 5:
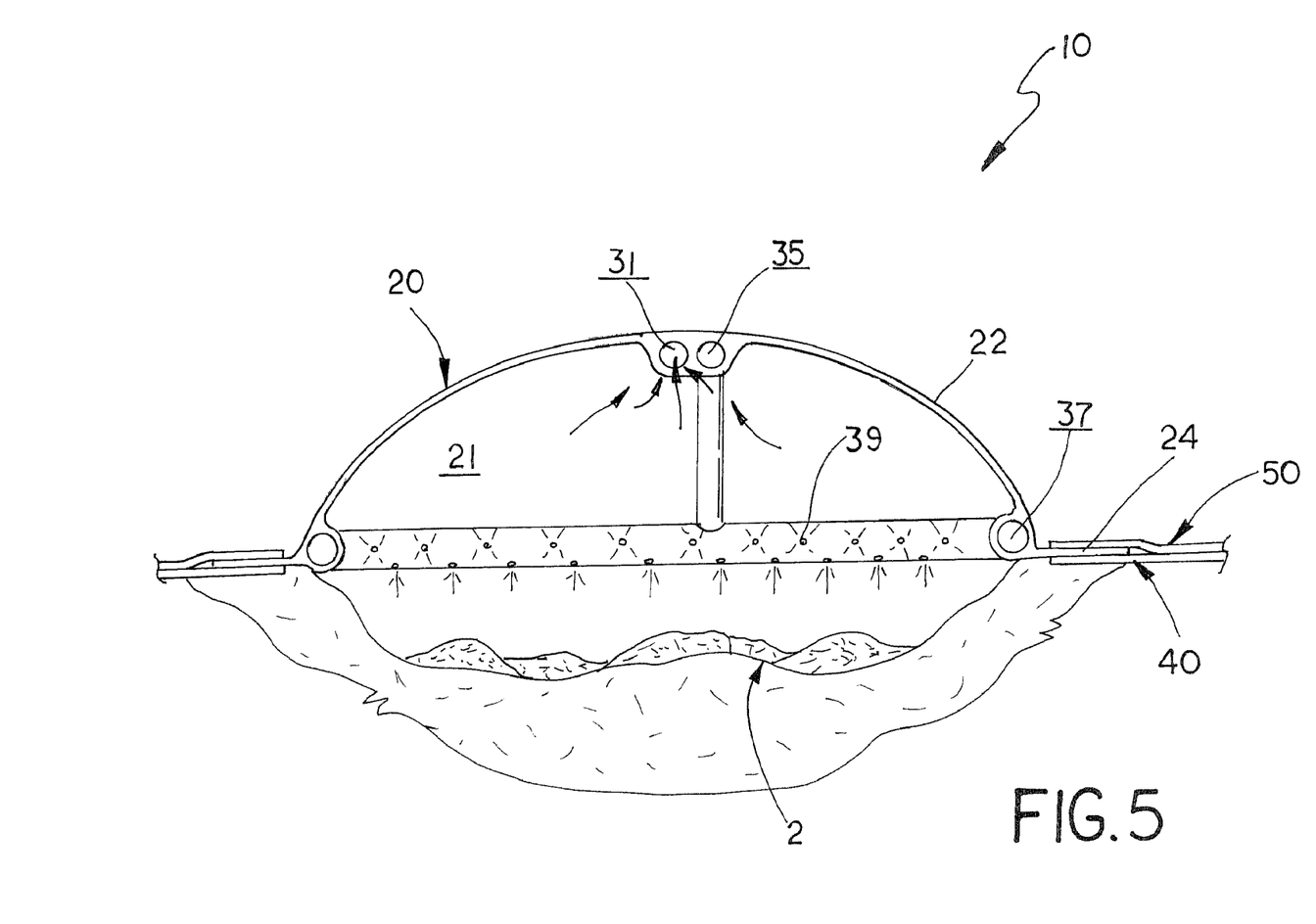
FIG. 5 is an end sectional view of the wound dressing apparatus taken along line 5-5 of FIG. 2.

A first end of second passage 35 may be adapted to connect to a positive pressure source and/or to lumen connector 32. A second end of second passage 35 is in open communication with the manifold 37. Second passage 35 may be adapted or arranged to extend across a portion of the domed chamber 22. In some embodiments, second passage 35 extends laterally from lumen connector 32 across dome center 22 to the manifold 37, as shown in FIG. 4. The structure of second passage 35 extending laterally over the domed center 22 from one side to the other lends structural integrity to the domed center, which helps prevent wound dome 20 from collapsing during negative pressure wound treatment.

Wound dome 20 also has a fluid manifold 37 that may be integrally formed with or between the bottom peripheral edge of domed center 22 and/or flange 24. In some embodiments, the manifold 37 may have an annular shape, which may be similar to the shape of the domed center 22. In some embodiments, manifold 37 has a plurality of apertures 39 that may be spaced along its length, as shown in FIGS. 2 and 3. The apertures allow for open fluid communication between the manifold and the dome interior 21. Further, the apertures allow fluid to be dispersed radially into the wound site through the manifold 37.

Figure 8:
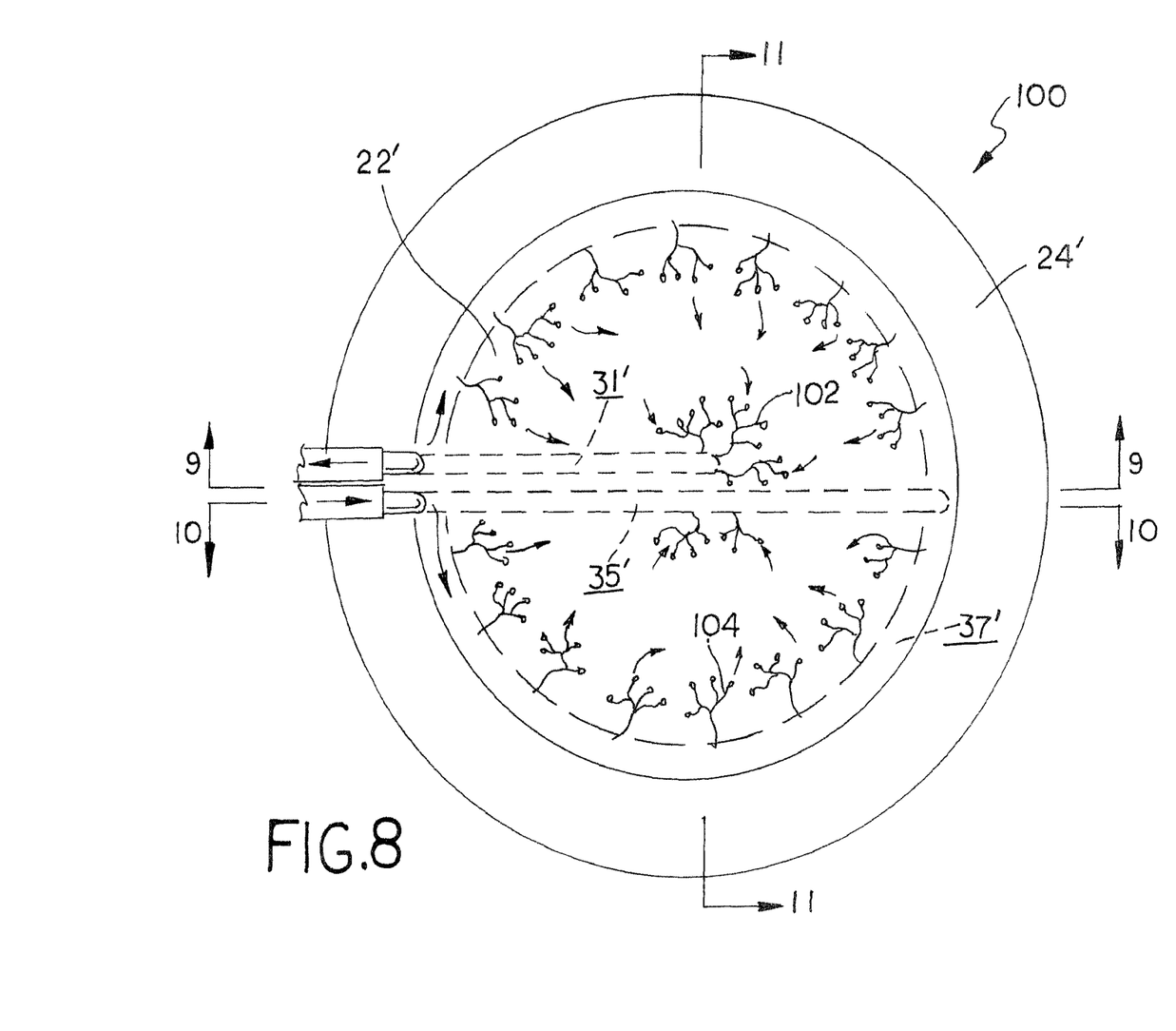
FIG. 8 is a top view of another embodiment of the wound dressing apparatus.

Similarly, as shown in FIGS. 8, 9, 10 and 11, in certain embodiments, the manifold 37' may include a plurality of branching channels, arteries or pathways 104 that are adapted to allow for open fluid communication between the manifold and the dome interior. In some embodiments, the branching channels 104 may be formed integrally with the wall of the domed center 22'. The branching channels 104 of the manifold may be arrange in a fractal pattern. Also, in various embodiments, the manifold 37 or 37' has an annular shape, and its length may span the circumference of the domed center 22 and/or of the dome interior 21, as shown in FIGS. 2 and 8.

Figure 6:
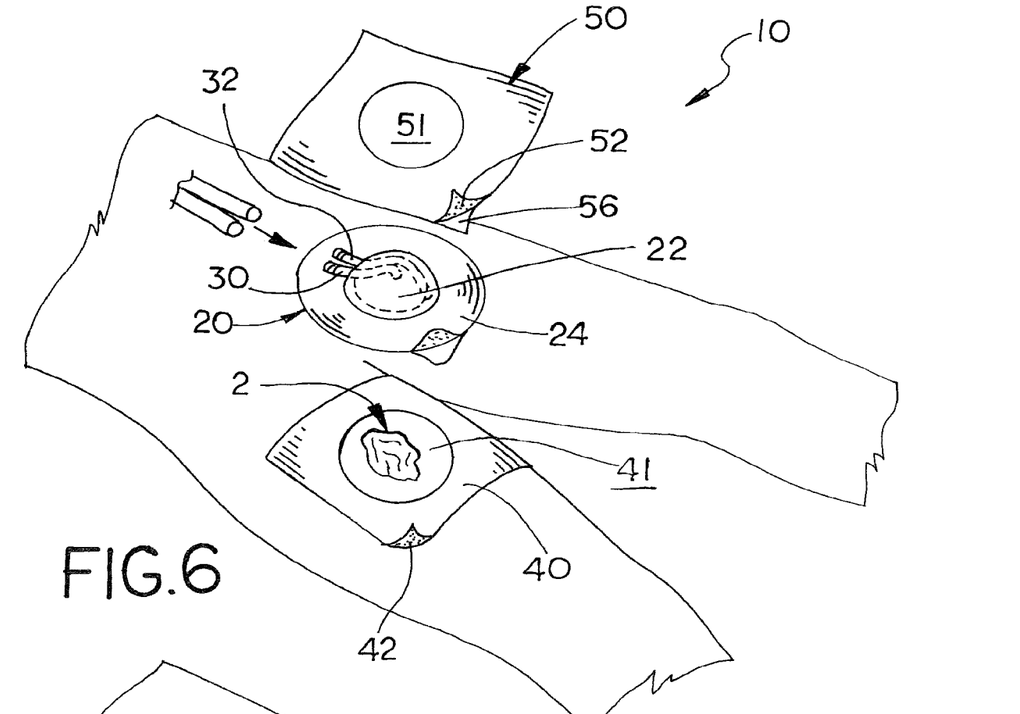
FIG. 6 is a perspective view of the wound dressing apparatus as applied to a wound site on a human leg.
Figure 7:
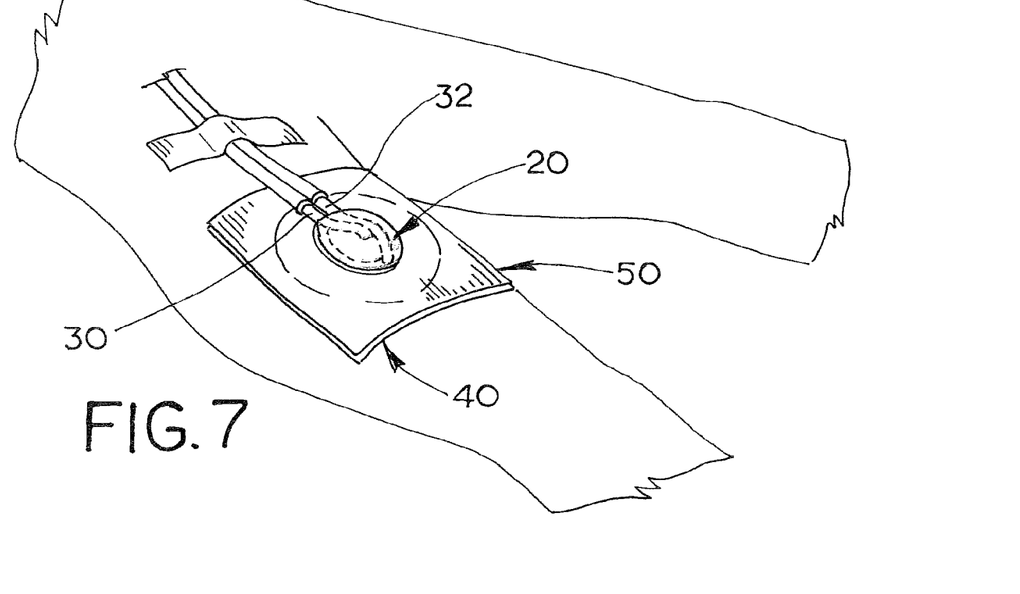
FIG. 7 is a perspective view of the wound dressing apparatus as applied to a wound site on a human leg.

As shown in FIGS. 1, 6 and 7, wound domed 20 may be sandwiched between two sealing drapes 40 and 50 when applied to a wound site 2. Sealing drapes 40 and 50 are of conventional design and construction, well known in the medical arts and are generally thin sheets of at least one sterile material that is not air permeable. As shown in FIG. 1 and in FIG. 6, each drape 40 and 50 may have an adhesive 42 and 52 on at least a portion of its surface. In some embodiments, adhesive is applied to at least a portion of a bottom surface of drape 40 and/or drape 50. The adhesive 42 and 52 may be covered by a disposable covering film 46 and 56, respectively.

Each of drapes 40 and 50 may be provided with a central opening, as shown in FIGS. 6 and 7, or the drape(s) may be cut to create opening(s) therein, as shown in FIG. 1. Drape 40 may be fitted over the wound site 2 with the drape opening 41 exposing the wound site. Drape 40 is secured to a subject's skin by its adhesive 42.

Wound dome 20 is placed over wound site 2 so that flange 24 contacts drape 40. An adhesive may be applied to at least a portion of flange 24, as desired, to seal and secure the flange to drape 40. In some embodiments, the bottom of flange 24 is coated with an adhesive. Drape 50 is placed over wound dome 20 so that domed center 22 extends through drape opening 51, as shown in FIGS. 6 and 7. Drape 50 is secured around wound dome 20 and to drape 40 by its adhesive bottom 52. Once wound dressing 10 is in place over wound site 2, the negative pressure lumen and positive pressure lumen are then connected to lumen connections 30 and 32.

Figure 10:
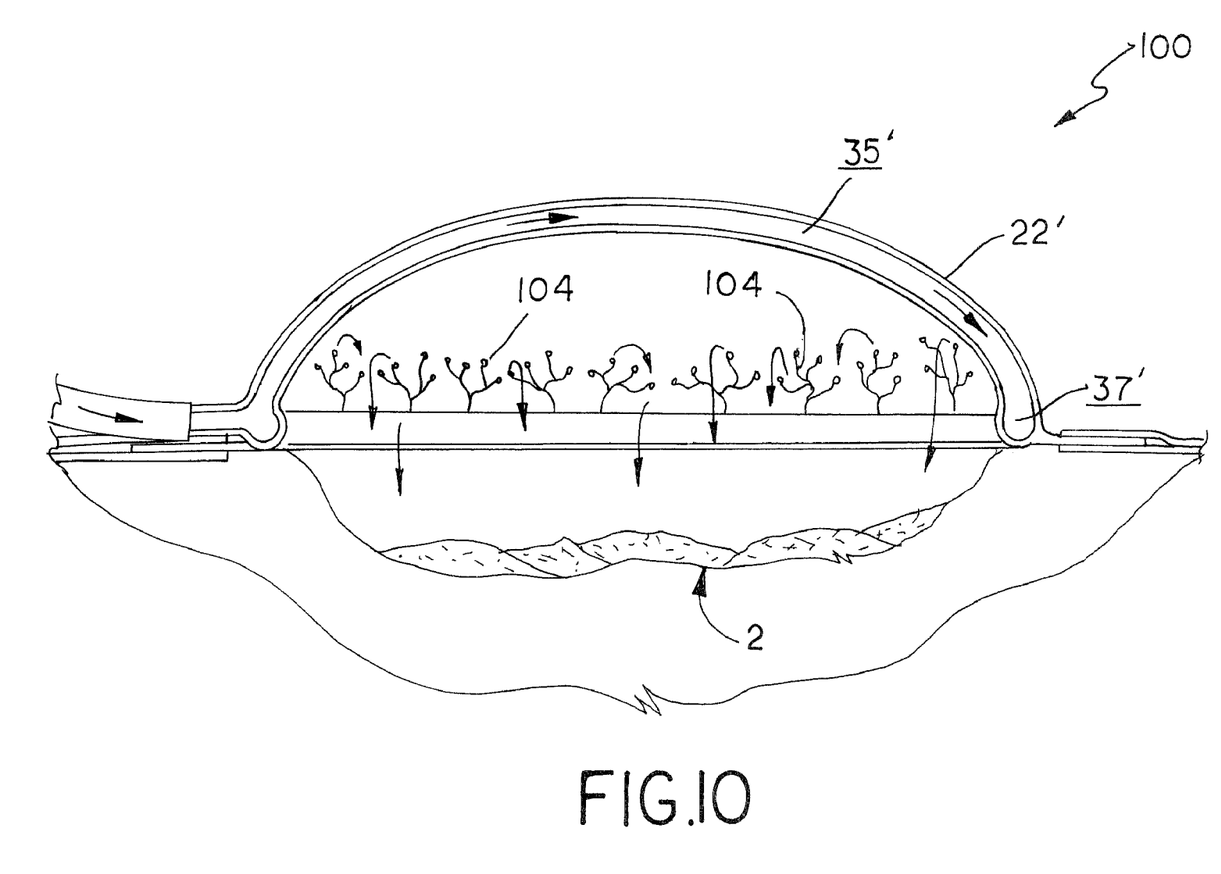
FIG. 10 is a sectional view of the wound dressing taken along line 10-10 of FIG. 8.

FIGS. 8-11 illustrate an alternate embodiment of the wound dressing apparatus. The alternate embodiment is designated as reference numeral 100. As shown in FIGS. 8-11, wound dressing 100 is configured to have a domed center chamber 22', including a chamber wall defining a dome apex, a substantially hollow dome interior, a peripheral edge, and a flange 24'. Wound dressing 100 employs principles of fractal fluid dynamics. As shown in FIG. 9, first fluid passage 31' extends across a portion of the dome center chamber 22' and opens at or proximate to the apex of domed center 22' into a series of smaller branching arteries 102 formed in the wall of domed center 22'. Similarly, manifold 37' has a plurality of branching arteries 104 formed in the wall of the domed center 22'. As shown in FIG. 10, second passage 35' is in communication with manifold 37'. Both sets of branching arteries are configured using fractal fluid dynamics to optimize fluid flow to first fluid passage 31' or manifold 37'. Each set of branching arteries 102 and 104 may be arranged in a fractal pattern.

In certain embodiments, the wound dressing apparatus is configured to provide both negative pressure wound treatment and positive pressure (e.g., hyperbaric oxygen) treatment to a wound site. The wound dressing apparatus may cover a wound site and may hermetically seal the wound site and facilitate the wound treatment. For example, the negative pressure and hyperbaric oxygen therapies may be delivered at therapeutic levels via a wound dressing apparatus using one or more operational modes.

Therapeutically effective levels of hyperbaric oxygen and negative pressure treatments may be affected by different combinations of fluid pressures, fluid concentrations, fluid flow rates, treatment durations, and treatment intervals, as is known in the art. For example, in some embodiments of the present invention, therapeutically effective wound treatment levels and wound treatment protocols can be determined generally in accordance with the methods and principles and described in U.S. Pat. Nos. 7,648,488, 8,357,130, U.S. Patent Publication No. 2008/0140029, and U.S. Patent Publication No. 2010/0121287, all of which are hereby incorporated in their entirety by reference.

An example of a wound treatment protocol combining the application of negative pressure and hyperbaric oxygen treatments can include administering hyperbaric oxygen therapy to the wound in a range of approximately 8 minutes to approximately 12 minutes and administering negative pressure therapy to the wound at less than 1 atmosphere for approximately 8 minutes to approximately 12 minutes. However, the wound treatment cycle times and ranges may vary according to the nature and severity of the wound being treated and according to the wound response to the treatment. The hyperbaric oxygen therapy and the negative pressure therapy are administered intermittently such that negative pressure therapy is administered immediately following the administration of hyperbaric oxygen therapy and hyperbaric oxygen therapy is administered immediately following the administration of negative pressure therapy. In this exemplar wound treatment protocol, the wound may be subject to an absolute pressure of from approximately 60 mmHg to approximately 160 mmHg during the administration of negative pressure therapy. Administering hyperbaric oxygen therapy may include supplying oxygen or humidified oxygen to the wound at a flow rate of approximately 0.1 liters per minute to approximately 3 liters per minute.

In a particular embodiment, the wound dressing apparatus facilitates both an internal negative pressure and a positive pressure wound therapy at a wound site. The wound dressing apparatus includes a pliable wound dome configured to have a hollow domed center, a flat integral peripheral flange and one or more integral lumen connectors. The lumen connectors are in open communication with two fluid passages that are formed within the walls of the domed center. An annular fluid manifold is integrally formed between the bottom edge of the domed center and the peripheral flange. A fluid passage may extend laterally across the dome center where it opens into the annular manifold. The manifold has a plurality of apertures spaced along its length, which allows for the even, radial delivery of fluid into the wound site. Another fluid passage extends partly over the dome center but terminates in an opening at the apex of the domed center, which allows fluids to be drawn radially from the center of the wound dome.

The embodiments of the invention provided herein described and illustrated are not intended to be exhaustive or to limit the invention(s) to the precise form(s) disclosed. Rather, they are presented to explain the invention(s) so that others skilled in the art might utilize its teachings. Indeed, it should be understood that the foregoing description is only illustrative of the invention. Various alternatives and modifications can be devised by those skilled in the art without departing from the invention. Accordingly, the invention is intended to embrace all such alternatives, modification and variances that fall within the scope of the invention. In addition, it should be understood that aspects of the various embodiments may be interchanged in whole or in part. For example, while specific embodiments of a wound dressing apparatus have been exemplified, other embodiments and uses are also contemplated herein. Therefore, the scope of the appended claims should not be limited to the description of the versions contained therein.

What is claimed is:

1. A wound dressing apparatus comprising:
   a domed chamber having a chamber wall defining a dome apex, a peripheral edge, and a substantially hollow dome interior;
   a flange extending away from the peripheral edge of the domed chamber;
   a manifold within the domed chamber, the manifold comprising a plurality of branching arteries, each artery terminating in multiple apertures in communication with the dome interior;
   a first passage having a first end adapted to connect to a negative pressure source and a second end in communication with the dome interior; and
   a second passage having a first end adapted to connect to a positive pressure source and a second end in communication with the manifold.

2. The apparatus of claim 1, wherein the manifold is formed integrally with the domed chamber.

3. The apparatus of claim 1, wherein the manifold is formed integrally with the flange.

4. The apparatus of claim 1, wherein the manifold has an annular shape.

5. The apparatus of claim 1, wherein the first passage extends partially across the chamber wall.

6. The apparatus of claim 1, wherein the second end of the first passage is connected proximate to the apex of the domed chamber.

7. The apparatus of claim 1, wherein a portion of the first passage is formed integrally with the domed chamber.

8. The apparatus of claim 1, wherein a portion of the second passage is formed integrally with the domed chamber.

9. The apparatus of claim 1, wherein the second passage extends across a portion of the domed chamber.

10. The apparatus of claim 1, wherein the chamber wall comprises a pliable material.

11. The apparatus of claim 1, wherein the chamber wall comprises silicone rubber.

12. The apparatus of claim 1, further comprising an adhesive provided on at least a portion of the flange.

13. The apparatus of claim 12, wherein the adhesive is effective to create a seal between the flange and a wound drape.

14. A wound dressing apparatus comprising:
   a domed chamber having a chamber wall defining a dome apex, a peripheral edge, and a dome interior;
   a flange extending away from the peripheral edge of the domed chamber;
   a manifold formed within the domed chamber, the manifold comprising branching arteries, each artery terminating in multiple apertures in communication with the dome interior;
   a first passage having a first end adapted to connect to a negative pressure source, the first passage comprising a plurality of channels in communication with the dome interior; and
   a second passage having a first end adapted to connect to a positive pressure source and a second end in communication with the manifold.

15. The apparatus of claim 14, wherein the first passage extends partially across a portion of the domed chamber.

16. The apparatus of claim 14, wherein the second passage extends across a portion of the domed chamber.

17. The apparatus of claim 14, wherein the manifold is formed integrally with the domed chamber.

18. The apparatus of claim 14, wherein the manifold spans the circumference of the dome interior.

* * * * *